United States Patent [19]

Ashmead

[11] Patent Number: 4,774,089

[45] Date of Patent: Sep. 27, 1988

[54] STIMULATION OF GONADOTROPIC HORMONES WITH MINERAL MIXTURES CONTAINING AMINO ACID CHELATES

[75] Inventor: Harvey H. Ashmead, Kaysville, Utah

[73] Assignee: Albion International, Inc., Clearfield, Utah

[21] Appl. No.: 744,923

[22] Filed: Jun. 14, 1985

[51] Int. Cl.$^4$ .................... A61K 33/08; A61K 37/14
[52] U.S. Cl. .................................. 424/157; 424/154; 514/6; 514/492; 514/494; 514/499; 514/502
[58] Field of Search ................. 514/6; 424/154, 157

[56] References Cited

U.S. PATENT DOCUMENTS 4,020,158  4/1977  Ashmead et al. ................ 514/6
4,167,564  9/1979  Jensen ............................. 514/6

Primary Examiner—Leonard Schenkman
Attorney, Agent, or Firm—Thorpe, North & Western

[57] ABSTRACT

A composition and method for stimulating gonadotropin hormone production and maintaining intracullar mineral balance in the reproductive organs of mammals. The composition consists of a mineral mixture containing effective amounts of manganese, iron and zinc as amino acid chelates in appropriate ratios. Preferable the composition also contains effective amounts of one or more minerals selected from the group consisting of copper, magnesium and potassium all of which are present at least in part as amino acid chelates or complexes. When magnesium and potassium are present at least some of these are present in inorganic form. Vitamins, other minerals such as calcium and phosphorus, and fillers may also be utilized.

The composition is orally administered to female mammals to both induce estrus and bring about a stronger and more noticable estrus. In the male both libido and spermatogenesis are improved by the oral administration of the composition.

21 Claims, No Drawings

STIMULATION OF GONADOTROPIC HORMONES WITH MINERAL MIXTURES CONTAINING AMINO ACID CHELATES

This invention relates to the stimulation of gonadotropin hormones in mammals through the administration of mineral mixtures containing amino acid chelates. More particularly, this invention relates to the inducing of ovulation in female and spermatogenesis in male mammals through the use of amino acid chelates.

It is documented that certain minerals in the hypothalamus and pituitary are correlated with gonadotropin secretion. Merriam et al, Sex-Related and Cyclic Variation of Trace Elements in Rat Hypothalamus and Pituitary, Brain Research, 171 (1979) 503–510, state that under hormonal manipulations, hypothalamic zinc concentration and gonadotropin secretion appear to be correlated. These researchers report that inorganic minerals such as copper, iron and zinc when administered as salts in high doses, and injected intravenously, or into the hypothalamus, induce ovulation in rabbits and rats. While these researchers found some variation in mineral concentrations during the estrus cycle of rats they were not able to reach any conclusions regarding the effect of trace minerals on this cycle. In fact, they conclude that while elevations of hypothalamic zinc appear to correlate with the release of gonadotropin releasing hormone and gonadotropins which occurs between proestrus and estrus, and after castration, this does not establish a casual relation. Also, the rise in copper at estrus cannot be similarly correlated because copper falls after castration when gonadotropins are elevated. They therefore conclude that they could not make a direct connection between physiological changes in copper and gonadotropin release.

While the presence of trace minerals in the hypothalamus and pituitary are of interest there are also other gonadotropic releasing substances which also are being discovered. Releasing factors or releasing hormones are being utilized on an increasing basis to stimulate, repair or maturate the sex organs. These releasing factors or hormones activate various hormones from the pituitary, or master gland, which in turn, serves the higher master gland, the hypothalamus. Researchers, as reported in Medical World News, Oct. 27, 1972, pp. 52–55 and 63–65, have found that the central nervous system controls the secretion of gonadotropic hormone from the pituitary gland in response to stimulation from the hypothalamus. Electrical stimulation of the hypothalamus resulted in ovulation in rabbits but the same stimulation to the pituitary did not produce the same results. Much research has shown that gonadotropic hormone release is affected by various central nervous system stimulating agents such as epinephrine, norepinephrine, catecholamine, dopamine, and histamine with pentobarbital.

The release of LH (luteinizing hormone), ACTH (andrenocorticotropic hormone), CRH (corticotropin-releasing hormone) and TRH (thyrotropin-releasing hormone), LRH (luteinizing-releasing hormone), FSH (follicle-stimulating hormone), and others have been studied. While extremely complicated, at least some of these hormones and/or releasing factors have been qualitatively identified as being sequences of amino acids. The TRH molecule has been isolated and found to contain just three amino acids-glutamic acid, histidine, and proline-in a peptide chain with the carboxyl terminal of this tripeptide being modified by a primary amine. CRH has been shown to consist of an amino acid sequence whose structure has not been fully worked out. Also LRH has been shown to be a decapeptide consisting of ten amino acids.

LRH has been found to induce ovulation in females and also increase sperm counts in males. However, one problem associated with it has been to find a practical method of administering it to mammals in order to obtain the desired response. Since minerals and amino acid sequences both appear to affect gonadotropin stimulation and release it would be beneficial to find a means for administering both to male and female mammals in optimum dosages in readily bioavailable form if the desired results in increasing reproductivity could be obained. Studies have shown that suboptimal reproductive performance in beef and dairy cattle is the second most limiting disease factor preventing a more efficient production of beef and dairy food products in the United States. A 1981 survey indicated that the annual economic loss on a national level was estimated at $1.3 billion or approximately $116 per cow. As a result of this loss and the increased costs of beef and dairy food products to the consumer caused by these inefficiencies, the solving of these problems with new research is very important.

OBJECTS AND SUMMARY OF THE INVENTION

It is an object of the present invention to provide a composition and method for the stimulation and release of gonadotropin hormones in male and female mammals. It is also an object of this invention to provide a composit and method for balancing the intracellular content of minerals in the hypothalamus, pituitary and sex organs of of males and female mammals to enhance and increase reproductivity.

Another object of this invention is to provide a composition and method of enchancing estrus in female mammals such that stronger and more viable heats are produced and conception rates are increased.

Yet another object of this invention is to provide a composition and method for improving spermatogenesis in male mammals.

These and other objects are accomplished through the appropriate administration of mineral mixtures containing amino acid chelates at appropriate times and amounts to both males and females of various mammal species.

It has been surprisingly found that the administration of at least iron, zinc and manganese as amino acid chelates often stimulates the absorption of other minerals even though such other minerals were not administered in the form of amino acid chelates. Preferably, a member of the group consisting of copper, magnesium and potassium will also be administered along with the iron, manganese and zinc amino acid chelates. The copper and at least a portion of the magnesium will be present as amino acid chelates and at least a portion of the potassium will be present as an amino acid complex. The remainder of the magnesium and potassium will be present in inorganic form, preferably as magnesium oxide and potassium chloride.

While the exact pathway of gonadotropin stimulus caused by administration of mineral mixtures containing amino acid chelates is not known it is believed that the polypeptide ligands utilized in forming the amino acid chelates function similarly to TRH by having their terminal carboxylate grouping modified by chelation to appropriate mineral cations. In addition, the polypeptide ligands function to allow the mineral ions to be absorbed intact as amino acid chelates into the bloodstream from which they are then distributed to appropriate biological tissues where they can function more effectively to maintain proper intracellular mineral balance and induce gonadotropin release than the large dosages of mineral salts utilized in prior art tests.

DETAILED DESCRIPTION OF THE INVENTION

It has now been found that by proper health management coupled with the appropriate administration of mineral mixtures containing amino acid chelates to mammals breeding efficiencies can be obtained resulting in increased production of various mammal species. Each female species might be expected to be treated somewhat differently due to differing estrus cycling times, gestation periods, length of lactation as well as environment. Thus, while the invention will be described in a general manner some variation may be necessary to make it optimal for any given species. However, the information provided herein will be sufficient that one having skill in the art will be able to apply the invention to males and females of any mammalian species even though some experimentation may be required.

Although it has been known for some time that the administration of amino acid chelates to mammals will result in increased absorption of metals into biological tissues it has not been established that estrus can be initiated, enhanced or synchronized or that spermatogenesis will result from the appropriate administration of amino acid chelates. Also, it has not been known that administration of mineral mixtures containing amino acid chelates will bring about intracellular mineral balance as distinguished from merely increasing the mineral content of the mineral in the amino acid chelate being administered.

Ashmead et al, U.S. Pat. No. 4,020,158, Ashmead, U.S. Pat. No. 4,076,803 and Jensen, U.S. Pat. No. 4,167,564 all teach that the use of amino acid chelates assist in increasing absorption of essential minerals into biological tissues and even across placental membranes into the foeti of gestating mammals. However, even though these patents teach increased metal content in tissues, better weight gain and overall health, there is no indication that amino acid chelates may be useful in the bringing about of the estrus cycle, enhancing the strength of estrus so as to increase the liklihood of conception or iniating the estrus cycle in dormant female mammals. Also there is no indication that spermatogenesis and increased libido may be brought about in male mammals.

The exact mechanism or mode by which these effects are attained is not known with certainty but there are certain requirements of the compositions to be administered and certain conclusions which can be drawn from the use of the compositions. It is believed that the molecular weight of the ligands utilized in preparing the amino acid chelates is important and possibly also the amino acid make-up. There has been insufficient research to date to verify the amino-acid content and sequences. However, it has been found that the combined molecular weight of the ligands comprising any one amino acid chelate should not exceed about 1000 and preferably not more than about 500. Particularly preferred are amino acid chelates wherein the ligand weight will not exceed about 300. The preferred amino acid chelates are those containing the metals zinc, manganese and iron wherein there are at least two ligands attached to the metal ion forming the chelate. It is preferred that each individual ligand have a molecular weight that does not exceed 500 and preferably will not exceed 150. It is therefore preferable that the ligands be limited to single amino acids or dipeptides at most. Particularly preferred are mineral mixtures containing amino acid chelated manganese, iron and zinc and also containing at least one additional mineral selected from the group consisting of copper, magnesium and potassium. Each additional mineral, when present, is present at least partially in amino acid chelated or complexed form. When magnesium and/or potassium are present it is advisable to administer additional amounts of magnesium and potassium in inorganic form, preferably as magnesium oxide and potassium chloride. Preferably manganese, iron, zinc, copper, magnesium and potassium will all be present in the formulation. The total mineral content is preferably formulated such that the ratios of magnesium to potassium, iron to zinc and iron to manganese will be at least 2:1. The ratio of zinc to manganese will be at least 1:1 and may be 2:1. The ratio of complexed potassium to chelated magnesium will be at least 2:1. About 15-50% of the potassium in the mixture may be in the form of a potassium amino acid complex with the remainder being inorganic. About 5-25% of the magnesium may be in the chelated from with the remainder being inorganic. When any of the above stated mineral pairs are present they will preferably be present in the above stated ratios even though all six minerals may not be utilized.

It may also be preferable to combine added amounts of cobalt and selenium to the formulation. The cobalt may be present in chelated or inorganic form as may the selenium. When cobalt is present in inorganic form it will usually be as the carbonate. Selenium may be utilized as sodium selenite.

It is believed that the amino acid chelates exert their influence on the hypothalamus and pituitary of mammals respectively to release gonadtropic hormones in much the same manner as the known polypeptide releasing factors in the pituitary such as LH, ACTH, TRH, LRH, FSH and the like. In TRH, for example, the molecule is a tripeptide of glutamic acid, histidine and proline with the carboxy terminal being modified by a primary amine. It is believed that the metal ion of the chelate acts similarly to modify free amino and carboxy groups of the ligands to maximize the hormone stimulating activity thereof. It is also believed that the amino acid ligands play an important role in transporting the appropriate minerals to the reproductive organs to provide intracellular mineral balance to the uterus, ovaries and testes of the mammals. One surprising aspect of the invention is the discovery that, by combining amino acid chelates with inorganic minerals, equivalent or even superior results are obtained in the enhancing of estrus and spermatogensis. Inorganic minerals are not as bioavailable as minerals chelated with amino acids. However, when mixtures of amino acid chelates and inorganic mineral salts or oxides are administered jointly, the mineral ions from the inorganic salts or oxides are more readily adsorbed than when administered alone. It is therefore within the scope of the invention to administer amino acid chelates along with inorganic minerals and, in addition, hydrolzyed proteins. When inorganic mineral salts and hydrolyzed proteins are mixed the same results are not obtained as when amino acid chelates and inorganic mineral salts are mixed.

Metals selected from the group consisting of magnesium, potassium, iron, manganese, zinc, copper, cobalt and selenium have been found to be beneficial to utilize in preparations for the bringing about and enhancing estrus and spermatogenesis. Of these, cobalt and selenium are often administered as inorganic salts or amino acid chelates. Magnesium and potassium may be utilized as inorganic salts or oxides or reacted with amino acids as previously described. Potassium does not react with a ligand to form a true chelate. Rather, a 1:1 ligand to metal complex is formed. It has been found beneficial to administer magnesium as a mixture of magnesium oxide and magnesium amino acid chelate and to administer potassium as a mixture of potassium chloride and potassium amino acid complex within the above described parameters.

The effectiveness of the composition is improved if other ingredients are also added. However, these could be administered separately. Sources for providing Vitamns A, D3, B12, E, K, Biotin, Riboflavin, Niacin, Thiamine, Calcium Panothenate, and Choline are beneficial to make sure that the animal is receiving a balanced vitamin and mineral preparation.

In addition, carriers such as salt, processed grain by products, condensed fish solubles, soybean meal, corn distillers dried grains or solubles, dicalcium phosphate, monosodium phosphate, hominy feed and cane molasses may be utilized to provide bulk, increase palatibility and add sources of partially hydrolyzed polypeptides, calcium and phosphorus.

The dosage may vary according to species, stage of development and breeding history. For example, a heifer or dry cow may be treated differently than a lactating cow or a pregnant cow which is to be bred as soon as possible after parturition. A cow which cycles regularly but has weak heats or which does not settle easily may be treated differently than a cow which cycles regularly and conceives readily.

In an embryo transplant program where donor and recipient cows must have synchronized heats, the dosage may be adapted to those specific needs.

In animals suspected of having specific mineral deficiencies it may be advisable to first assay the hair or biopsied tissues of these animals for mineral content as suggested in U.S. Pat. No. 4,020,158 and first treat those animals with amino acid chelates containing the deficient mineral. That treatment is separate and distinct from the present invention.

To induce, enhance, synchronize or otherwise affect estrus and/or spermatogenesis it has been found that a combination of iron, manganese and zinc are preferably present in the form of amino acid chelates. Also, preferably one or more metals selected from the group consisting of copper, magnesium and potassium will also be present. Particularly preferred are compositions containing all six of these minerals within the above described ratios. Again, part of the magnesium and potassium can be present in inorganic form such as magnesium oxide and potassium chloride. The potassium and chloride ions are believed to play an important role in the regulation of the intracellular potassium, sodium and chloride balance of the animals sex organs. Manganese is also an important mineral regulating the functioning of the sex organs.

The other minerals are believed to in some way cooperate with the amino acid ligands in triggering the release of the gonadotropic hormones to bring about the desired results.

Since the estrus cycle varies from mammal species to species it is not possible to formulate one set composition to accomplish desired results. However, from the data presented one having ordinary skill in the art will be able to formulate optimal compositions for each species.

Dosages are not strictly determined because most of the compositions are administered in the feed of the animal being treated. Therefore, general dosages based on an average of how much a treated animal will eat in any given day are often utilized. How much an animal will seat will also depend upon many extrinsic factors such as temperature, exercise, palatability of feed, etc. It is much more important that the ratios of minerals be maintained than that a specific dosage be administered as long as the animal is recieving effective amounts of each mineral. Generally speaking an effective dosage of magnesium may vary between about 1.5 and 35 mg/kg of body weight. Potassium may vary between about 1.2 and 33 mg/kg of body weight. Other minerals are usually present in smaller amounts. Iron will generally vary between about 0.1 and 25 mg/kg of body weight. Zinc will vary between about 0.1 and 12 mg/kg of body weight. Manganese is generally present in amounts between about 0.04 and 5 mg/kg of weight. Copper is present in amounts ranging from about 0.005 to 0.5 mg/kg. Cobalt and selenium, when present are present in much smaller trace amounts. These may also vary according to species. Swine, for example, may require more iron whereas cattle may require more magnesium.

Because data on cattle is most abundant the bovine species will be primarily utilized in illustrating the effectiveness of the invention. However, data on swine will also be presented.

The invention may be utilized at any desired time during a cow's reproductive life or during her reproductive cycle. It may be utilized on dry cows or growing heifers to bring about and produce strong estrus. It may be utilizsed during gestation and after parturition to promote rebreeding and minimize the number of services required for settling to take place. In addition, it may be given to a lactating non-gravid cow to stimulate and bring about estrus. Each case may require different dosages and/or treatment. The same reasoning also applies to other female mammal species. The time and dosage required to improve spermatogenesis in male mammals will also vary from species to species. However, by following the above mentioned ratios and effective amounts the optimum number of minerals to administer, their ratios to each other, dosage amount, and length of administration can be readily determined by those skilled in the art to which this invention pertains.

EXAMPLES

In demonstrating the viability of the present invention three basic formulations were utilized for feeding to cattle and swine species and are listed below. The potassium complex was a 1:1 amino acid ligand to potassium ion ratio and the amino acid chelates were at least 2:1 amino acid ligand to metal ion ratios. Each ligand had an average molecular weight of about 150 and was obtained by the hydrolysis of low salt soy protein isolate.

Composition A: 10.0% w. magnesium oxide, 6.0% w. potassium chloride, 0.689% w. magnesium as magnesium amino acid chelate, 1.227% w. potassium as potassium amino acid complex, 0.795% iron as iron (ferrous) amino acid chelate, 0.161% w. manganese as manganese amino acid chelate, 0.401% w. zinc as zinc amino acid chelate, 0.022% w. copper as copper amino acid chelate, processed grain by-products, condensed fish solubles, soybean meal, vitamin A supplement, vitamin D3 supplement, vitamin B12 supplement, vitamin E supplement, menadione dimethylpyrimidinol bisulfite (source of vitamin K), biotin, riboflavin, niacin, calcium pentothenate, thiamine hydrochloride, choline chloride and cane molasses.

Composition B, 25.0% w. dicalcium phosphate, 3.25% w. monosodium phosphate, 4.75% w. magnesium oxide, 3.25% w. potassium chloride, 0.178% w. magnesium as magnesium amino acid chelate, 0.674% w. potassium as potassium amino acid complex, 0.343% iron as iron (ferrous) amino acid chelate, 0.069% w. manganese as manganese amino acid chelate, 0.173% w. zinc as zinc amino acid chelate, 0.0094% w. copper as copper amino acid chelate, 0.003% w. cobalt as cobalt carbonate, 0.4% w. sodium selenite, salt, corn distillers dried grains, corn distillers dried solubles, vitamin A supplement, vitamin D3 supplement, vitamin B12 supplement, vitamin E supplement, menadione dimethylpyrimidinol bisulfite (source of vitamin K), biotin, riboflavin, niacin, calcium pantothenate, thiamine hydrochloride and choline chloride.

Composition C: 10% w. iron as iron amino acid chelate, 5% w. zinc as zinc amino acid chelate, 2% w. manganese as manganese amino acid chelate with the remainder being hydrolyzed soy protein.

EXAMPLE I

Composition A was force fed to 55 Holstein cows which had an average calving interval of 16.5 months. These cows were not settling and had poor heat activity. Three ounces of Composition A was fed per head per day for 30 days prior to calving and then the amount was doubled to 6 ounces from calving to breeding. In addition 25 lbs. of Composition A was mixed with 25 lbs of salt and 50 lbs of a Ca:P mineral mix and fed free choice to the cows also. Over a test period of several months the calving interval had been reduced from 16.5 to 12.5 months, stronger heats were observed in the cows and over 50% of them had exhibited a first estrus within 7-10 days after freshening.

EXAMPLE II

A mixture of 25 lbs of Composition A, 50 lbs of a Ca:P mineral mix and 25 lbs salt was free fed to 18 Holstein heifers that were 21 to 35 months of age, weighed over 1250 lbs and had not been bred. Twelve heifers showed a strong estrus between 7 to 10 days after the feeding was started, four cycled between 21 and 35 days and one cycled 56 days after starting the program. Seventeen of the eighteen heifers settled on the first service.

EXAMPLE III

A herd of 111 pure bred cows were utilized in this study. This herd was selected because they had a reputation of being extremely fertile. They were fed a mixture of 50% Compsition A and 50% salt and fed free choice. All of these cows cycled between the 30th and 45th day after calving. All exhibited very strong heats and were artificially inseminated. Ninety-two of these cows (82.88%) settled on the first service, fifteen on the second service and the remaining four on the third service. This was the highest conception that had occurred on this farm in 13 years of cattle production.

EXAMPLE IV

Forty dairy cows which all had a history of breeding problems were selected from a herd. Thirty days prior to freshening these cows were put on a ration containing 3 ounces per day of Composition A. From freshening to breeding the ration of Composition A was doubled to 6 ounces per head.

It was observed that these cows showed stronger heats, settled better and quicker than previously and that the calving interval was significantly shortened. All forty cows settled with 28 settling on first service. Seven cows were bred at 57-75 days after calving, 21 cows were bred 75-90 days after calving and 12 cows were bred after 90 days.

EXAMPLE V

Six bulls whose semen was collected for artificial insemination purposes were placed on four ounces per head per day of Composition A and three ounces per head per day of Compositon C. After six weeks on the program there were no noticable differences in semen collection. The ration of Composition A was then raised to six ounces per day and Compositon C was raised to four ounces per day. Within a matter of days four of the six bulls showed increased libido and started collecting semen twice a week rather than once. One of the bulls had always produced deformed sperm-heads which was felt to be genetic. However, along with increaded libido, he started producing normal sperm.

These bulls were taken off their rations of Compositions A and C and regressed to their normal semen production. When the rations were placed back their increased libido and sperm collection returned.

This program was then tried on thirty seven bulls which were producing 80% processed semen. After being placed on the program the processed semen increased to 93%.

EXAMPLE VI

An 8 year old Simmental bull had quit producing semen for over a year. The condition was deemed to be an infection with scar tissue in the seminal vesicles. One vesicle was completely plugged and the other was almost closed. Medical advice was that there was no hope for future semen collection. Antibiotics were tried with no results and surgery was ruled out because of the amount of muscle and the fact that the bull weighed over 2600 lbs. The testicles appeared to be degenerating and the bull kicked at his penis when he urinated or when semen collection was attempted.

This bull was placed on an antibiotic at 1 mg. per b of body weight per day and placed on 4 ounces each of Compositions A and C.

After about 60 days on the program semen was collected and produced 55% live mobile sperm but still had puss cells in the semen. The testicles became more distinct and the bull stopped kicking at his penis when he urinated or semen collection was attempted. Regular semen collection was started and over the next five months 30-50% live sperm was detected in the semen. The infection cleared up but the semen was still not potent enough to freeze thaw.

The bull was placed in a barn on sand with fans on him, he was turned out to exercise a night one hour before sundown and exposed at a fence line to cows. Four months later he was producing 30 cc of 70% plus mobile sperm which survived the freeze thaw cycle. This was the best quality sperm ever collected from this bull.

EXAMPLE VII

For comparative purposes the semen from one bull was collected and analyzed for mineral content. Immediately after the first collection the bull was placed on a combination consisting of 6 oz. of Composition A and 2 oz. of Composition C per day. A second semen collection was taken after 60 days and also analyzed for mineral content. The following data is a composite of the analytical results reported in terms of percent of total mineral content:

|  | 1st collection | 2nd collection |
| --- | --- | --- |
| Sodium | 7.16 | 6.78 |
| Magnesium | .64 | .46 |
| Aluminum | 10.25 | 10.20 |
| Phosphorus | 25.76 | 27.65 |
| Sulfur | 18.44 | 15.38 |
| Chlorine | 4.58 | 7.61 |
| Potassium | 13.01 | 18.72 |
| Calcium | 12.85 | 3.03 |
| Chromium | .24 | .56 |
| Manganese | .31 | .65 |
| Cobalt | — | .33 |
| Iron | 3.36 | 3.96 |
| Nickel | .68 | 1.64 |
| Copper | 2.24 | 1.79 |
| Zinc | 1.32 | .54 |

The sperm from the second collection was of much better quality and more motile than that first collected. The correlation between the mineral content and sperm quality is not known for a certainty. However, it is believed significant that the ratio of chloride to sodium and potassium is higher in the sperm of the second collection and also that the calcium content has been greatly reduced.

It is also significant to note that the administration of the amino acid chelates and inorganic minerals did not necessarily result in an increase in metal content in the sperm cells. Rather, there was a mineral content ratio adjustment. It is believed that proper ratios enabled by the administration of the chelated and inorganic minerals contributed to increased sperm quality.

EXAMPLE VIII

A field evaluation of Composition C on English White Swine was conducted with a control group being fed a regular feed ration and a test group being given the same feed ration containing two kilograms of Compositon C per 2200 lbs. of feed. The feed consumption per head of swine averaged about 6 lbs/day. This feed was administered during the last six weeks of gestation. Upon farrowing the amount of Composition C in the feed was doubled and fed at that higher rate until weaning and rebreeding. The swine given composition C in their feed came into their first estrus within 5 days after weaning and had a conception rate on first breeding of about 94%. The control swine came into estrus on the average of 7.5 days after weaning and had a first service conception rate of about 73%. Records were kept on the litters which were farrowed from the control and treated sows with the following results:

|  | Control | Treated |
| --- | --- | --- |
| No. Litters | 126 | 125 |
| No. Piglets Born/Litter | 11.06 | 11.84 |
| No. Piglets Born Alive/Litter | 10.17 | 11.06 |
| No. Piglets Born Dead/Litter | 0.89 | 0.78 |
| No. Piglets Weaned/Litter | 8.71 | 9.36 |
| Ave. Weight/Piglet Born Live(Kg.) | 1.52 | 1.41 |
| Ave. Weight/Piglet Weaned(Kg.) | 5.10 | 5.08 |
| Ave. Weight Gain/Piglet(Kg.) | 3.58 | 3.67 |
| Ave. Age at Weaning(Days) | 21.4 | 20.5 |
| Ave. Daily Weight Gain(Kg./Day) | 0.167 | 0.179 |

It will be noted that there were statisically significant higher numbers of piglets born and born alive among the treated group and more piglets were weaned among the treated group.

Mortality from birth to weaning was slightly higher with the treated group and weights at birth were slightly lower. However, total litter weights were similar. Piglet weights at weaning were also similar; however, due to increased numbers of piglets per litter in the treated group the litter weaning weights were significantly higher.

This study showed that supplementation of the feed ration with Composition C resulted in almost 1 more piglet being born per litter and, although mortality was slightly higher in the treated group, there was an average of about 0.65 piglets/litter that were weaned. This figure correlates with data obtained from utilizing commercial iron injections in litter weights at weaning. However, in the case of iron injections the higher litter weights are a result of lower piglet mortality whereas, in the present case, the higher weights results from an increased number of piglets per litter.

On a commercial basis the data shows that a sow fed a treated feed ration is more able to support the growth of a larger number of piglets which would result in an increase of about 1.4 piglets/sow/year.

EXAMPLE IX

A second study was conducted on York Cross Swine utilizing 140 lbs of Composition A admixed with one ton of the regular feed ration in the treated group. During the last month of gestation the control and treated feed rations were fed at the rate of 8 lbs/sow/day. After farrowing and through rebreeding the feed rations were increased to 14 lbs/sow/day.

As in Example VII the sows feed the treated rations cycled earlier after weaning than the control sows and had a higher first conception rate. Exact data on this is not available. Data was kept on the litters from each group which are as follows:

|  | CONTROL | TREATED |
| --- | --- | --- |
| Litters Farrowed | 161 | 56 |
| Piglets Born Alive | 1707 | 653 |
| Ave. Piglets/Litter | 10.60 | 11.66 |
| Piglets Born Dead | 24 | 31 |
| Piglets Born Dead/Litter | .149 | .55 |
| Healthy Piglets Born | 1449 | 553 |
| Healthy Piglets Born/Litter | 9.0 | 9.87 |
| Average Litter Weight (lbs) | 25.93 | 29.16 |
| Average Piglet Birth Weight (lbs) | 2.45 | 0.50 |
| Ave. No. Piglets Weaned/Litter | 7.44 | 8.93 |
| Ave. Litter Weight at 35.75 days (lbs) | 100.57 | 141.93 |
| Ave. Daily Wt. Gain From Birth | .378 | .444 |

-continued

|  | CONTROL | TREATED |
|---|---|---|
| (lbs) | | |
| Ave. Weight of Pig at 35.75 days | 13.5 | 15.89 |
| (lbs) | | |

It is evident from the above that the treated sows produced more piglets per litter and that the piglets from the treated group gained weight more rapidly than the controls.

EXAMPLE X

A study is made to determine ovulation and embryo survival in dairy cows fed with Composition B as compared to the same mineral level administered only as inorganic minerals. The intracellular mineral levels in the uterine horns and body and their relationship to ovulaltion and affect on embryos are monitored. Also, endometrial histophatology and levels of intracellular minerals in the endometrium upon implantation of embryos and full term pregnancy are determined. Further, the relationship of mineral and hormone levels (progesterone and estrogen) in blood serum to intracullular levels of minerals in uterine tissues and embryos and to ovulation are compared.

One hundred fifty dairy heifers approximately 12 months of age are divided equally into three groups. Each group is maintained in similar environments and managed equally. The animals are acclimatized for 12 days during which time a base line study is done which includes blood analyses for mineral levels, rectal examinations of the reproductive organs and uterine biopsies on 10 animals to determine mineral levels and histopathology.

The animals are divided into three groups of 50 heifers each and fed as follows:

Group I—Each heifer is fed 4 oz/day of Composition B. The feeding is continued for 180 days or until the animal has been diagnosed pregnant via rectal palpation. Composition B is fed in addition to a regular balanced diet with the regular mineral mix requirements for yearling heifers.

Group II—Each heifer is fed the equivalent to

Composition B in inorganic minerals for the same 180 day period, or until confirmed pregnant by rectal palpation. The same balanced diet is utilized as with Group I.

Group III—Each heifer is fed the balanced diet used with Groups I and II but without adding any extra minerals in either chelated or inorganic form.

Daily observations are made for estrus detection and strength of the estrus cycle during the study and until final pregnancy is confirmed by rectal palpation.

Sixty days after commencing the study, rectal examinations are done on each reproductive tract and ovarian structure of each heifer. The examinations start 15 days after each heifer shows an active estrus and continue at 2 day intervals until a preovulatory follicle is detected on an ovary. Routine rectal examinations are done on each animal on a weekly basis. Detailed recordings of the findings are maintained.

Three heifers from each group are prepared for superovulation simultaneously using the follicle stimulating hormone (FSH) and prostaglandin F2a (PGF2a) treatment starting on day 10 considering estrus to be day 0. These heifers are bred using conventional artificial insemination (A.I.) one half day after observation of first standing estrus. The inseminations are repeated twice about 12 hours apart. Estrus occurs 48 hours after the PGF2a injection on day 13.

Six to eight days after breeding the embryos from these heifers are flushed using the conventional gravity flow technique. Each embryo is classified as poor, fair, good and excellent by microscopic examination and placed in groups according to class and the uterine horn from which it was obtained. Each embryo is frozen for storage and/or further examination. The quality of embryos from each group is evaluated in relationship to the presence and concentrations of minerals in both the embryos and the ipsilateral uterine horn.

Blood samples are taken from the caudal or jugular veins of the heifers three times weekly for seven weeks during the study and tested by conventional radioimmunoassay producures for progesterone and estrogen levels. Blood samples are also taken to determine mineral levels in serum on the same dates as uterine biopsies are taken or embryos are collected.

The uterine biopsies are collected from each horn and body of the uetrus from each animal for histopathology and determination of intracellular mineral levels when the first preovulatory follicle is determined by rectal palpation following an initial 60 period of the study. Samples are also taken at the time of flushing the embryos after superovulating and breeding each animal in the three groups. Samples are also taken at the preovulatory stage of the estrus period as determined by rectal palpation prior to the estrus period that A.I. will be planned for full term palpation.

Two biopsies are collected at each sampling from the three uterine sites. One biopsy is fixed in 10% formalin and processed for histopathology. The second biopsy is frozen at −20 C.; and analyzed for intracellular mineral levels according to electron microscope x-ray microanalysis techniques.

The results from the study are not complete but data from a preliminary study show that ovulation of the follicles is disrupted when variations in concentrations of manganese, sodium, potassium and chloride occur in the uterine tissues. When follicles do not ovulate on an ovary, that ovary usually becomes inactive and small, while the opposite ovary becomes active, developes follicles and ovulates on subsequent estrus cycles.

The endometrium of the heifers in Group I show less pathology as compared to those in Groups II and III. The uterus involuted more readily as evaluated by sequential rectal examinations in Group I animals and it appears that inflammation of the endometrium is significantly reduced by providing optimal intracellular concentrations of minerals. Stated differently, it appears that optimal intracellular concentrations of minerals produce optimal intracellular metabolism and, in turn, reduces inflammatory and hypersensitivity reactions with reproductive tissues.

Of particular interest in the results is that manganese deficiency in the uterine tissues appears to prevent ovulations. Of the animals comprising Group I there is more manganese in the uterine tissues and the ratio of chloride to sodium and potassium is greater. The heifers of Group I have less pathology in the endometrial tissues and the overall reproductive health (involution and equality of pregnant vs. non-pregnant horns) improves more quickly in these animals than those in Groups II and III.

Estrus in the animals of Group I is stronger and more easily detected and the conception rate is improved.

The embryos flushed from the heifers of Group I are superior in both quality and number.

These examples show that reproductivity in mammnals may be enchanced through the administration of mineral mixtures containing amino acid chelated minerals. The time period to enhance spermatogenesis may vary from animal to animal. To obtain best results the mineral mixtures should be administered to the male animals well in advance of the breeding season. For bulls as an example it will take about 60 days for noticable consistant improvement to take place. For smaller animals the time may be shorter but it is recommended that treatment begin at least 30 days prior to semen collection or service.

For pregnant females it is desirable to begin treatment prior to parturition and continue it through weaning and estrus cycles until pregnancy is again confirmed. For non-pregnant animals the treatment may begin at any time and the female monitored for estrus which will usually be brought about with a matter of days after treatments begin. Administration of the mineral mixture may be carried out as long as desired and at least until pregnancy is confirmed.

The above examples are illustrative only and are not determinative of the scope of the invention which is limited only by the following claims.

I claim:

1. A composition for stimulating the production of gonadotropic hormones in mammals comprising a mineral mixture containing effective amounts of each of the minerals manganese, iron and zinc in chelated form said minerals being chelated with ligands selected from the group consisting of naturally occuring amino acids and dipeptides and tripeptides thereof said ligand to mineral mole ratio being at least 2:1 and wherein the molucular ratio of iron to zinc and iron to manganese is at least 2:1 and the molecular ratio of zinc to manganese is at least 1:1 and additional minerals magnesium, potassium and copper wherein the copper is in the form of a chelate chelated with a ligand selected from the group consisting of naturally occuring amino acids and dipeptides and tripeptides thereof having a ligand to copper mole ratio of at least 2:1, wherein the magnesium is in the form of a mixture consisting of magnesium in the form of a chelate with a ligand selected form the group consisting of naturally occuring amino acids and dipeptides and tripeptides thereof having a ligand to magnesium mole ratio of at least 2:1 and an inorganic magnesium compound and wherein the potassium is a mixture consisting of potassium in the form of a complex complexed with a ligand selected from the group consisting of naturally occuring amino acids and dipeptides and tripeptides thereof having a ligand to potassium mole ratio of 1:1 and an inorganic potassium compound wherein the molecular weight of each ligand in each chelate does not exceed 500 and wherein the total molecular weights of ligands forming each chelate do not exceed 1000 and wherein the molecular ratio of magnesium to potassium is at least 2:1.

2. A composition according to claim 1 wherein 5 to 25% by weight of the magnesium is present as a chelate with the remainder of the magnesium being present as magnesium oxide and wherein 15 to 50% by weight of the potassium is present as a complex with the remainder being present as potassium chloride.

3. A composition according to claim 2 which contains additional ingredients selected from the group consisting of vitamins, inorganic minerals and animal feed fillers.

4. A composition according to claim 3 containing inorganic minerals wherein the inorganic minerals are selected from the group consisting of cobalt carbonate, sodium selenite, dicalcium phosphate and monosodium phosphate.

5. A composition according to claim 3 containing animal feed fillers wherein the animal feed fillers are selected from the group consisting of processed grain by products, condensed fish solubles, soybean meal, corn distillers dried grains, corn distillers dried solubles, hominy feed, cane molasses and sodium chloride.

6. A composition according to claim 3 containing vitamins wherein the vitamins are selected from the group consisting of calcium panothenate, vitmin A, vitamin D3, vitamin B12, vitamin E, vitamin K, biotin, riboflavin, niacin, thiamine, choline chloride and sources thereof.

7. A composition according to claim 2 wherein the total molecular weights of ligands forming each chelate do not exceed 500 and wherein each ligand is a member selected from the group consisting of an amino acid or a dipeptide.

8. A composition according to claim 7 wherein the total molecular weights of ligands forming each chelate do not exceed 300.

9. A composition according to claim 8 wherein the molecular weight of each ligand does not exceed 150.

10. A method for stimulating the production of gonadotropic hormones in mammals which comprises administering to said mammals a composition comprising a mineral mixture containing effective amounts of each of the minerals manganese, iron and zinc in chelated form said minerals being chelated with ligands selected from the group consisting of naturally occuring amino acids and dipeptides and tripeptides thereof said ligand to mineral mole ratio being at least 2:1 and wherein the molecular ratio of iron to zinc and iron to manganese is at least 2:1 and the molecular ratio of zinc to manganese at lest 1:1 and an additional mineral selected from the group consisting of magnesium, potassium and copper and mixtures thereof wherein the copper is in the form of a chelate chelated with a ligand selected from the group consisting of naturally occuring amino acids and dipeptides and tripeptides thereof having a ligand to copper mole ratio of at least 2:1, wherein the magnesium is in the form of a mixture consisting of magnesium in the form of a chelate chelated with a ligand selected from the group consisting of naturally occuring amino acids and dipeptides and tripeptides thereof having ligand to magnesium mole ratio of at least 2:1 and an inorganic magnesium compound and wherein the potassium is a mixture consisting of potassium in the form of a complex with a ligand selected from the group consisting of naturally occuring amino acids and dipeptides and tripeptides thereof having a ligand to potassium mole ratio of 1:1 and an inorganic potassium compound wherein the molecular weight of such ligand in each chelate does not exceed 500 and wherein the total molecular weights of the ligands forming each chelate do not exceed 1000 and wherein the molecular ratio of magnesium to potassium is at least 2:1.

11. A method according to claim 10 wherein 5 to 25% by weight of the magnesium is present as a chelate with the remainder of the magnesium being present as magnesium oxide and wherein 15 to 50% by weight of the potassium is present as a complex with the remainder being present as potassium chloride.

12. A method according to claim 11 wherein the dosage of each mineral is present in amounts to provide a daily intake per animal in terms of milligrams per kilogram of bodyweight of between about 1.5–35 mg. magnesium, 1.2–33 mg. potassium, 0.1–25 mg. iron, 0.1–12 mg. zinc, 0.04–5 mg. manganese and 0.005–5 mg. copper.

13. A method according to claim 12 wherein the composition is orally administered to a male species to enhance spermatogenesis.

14. A method according to claim 12 wherein the composition is orally administered to a female species for a sufficient time to induce and enhance estrus.

15. A method according to claim 14 wherein the composition is orally administered to a lactating female and administration is continued until pregnancy is confirmed.

16. A method according to claim 14 wherein the composition is orally administered to a non-lactating female and administration is continued until pregnancy is comfirmed.

17. A method according to claim 14 wherein the composition is administered to a pregnant female during the last portion of pregnancy and continued post parturition until a new pregnancy is confirmed.

18. A method according to claim 17 wherein the amount of compositon administered post parturition is greater than the amount administered preparturition.

19. A method according to claim 11 wherein the total molecular weights of the ligands forming each chelate do not exceed 500.

20. A method according to claim 19 wherein the total molecular weights of ligands forming each chelate do not exceed 300.

21. A method according to claim 20 wherein the molecular weight of each ligand does not exceed 150.

* * * * *